United States Patent [19]
Terranova et al.

[11] Patent Number: 5,980,585
[45] Date of Patent: Nov. 9, 1999

[54] COMPOSITIONS FOR DYEING KERATINOUS FIBERS COMPRISING IMIDAZOPYRIDINE DERIVATIVES AND PROCESS

[75] Inventors: Eric Terranova, Bois Colombes; Aziz Fadli, Chelles; Alain Lagrange, Coupvray, all of France

[73] Assignee: L'Oreal, Paris, France

[21] Appl. No.: 09/212,565

[22] Filed: Dec. 16, 1998

[30] Foreign Application Priority Data

Dec. 16, 1997 [FR] France ................................. 97 15946

[51] Int. Cl.$^6$ ....................................................... A61K 7/13
[52] U.S. Cl. ......................... 8/409; 8/407; 8/408; 8/423; 8/568; 8/573
[58] Field of Search ................................ 8/407, 408, 409, 8/410, 423, 568, 573; 546/121

[56] References Cited

FOREIGN PATENT DOCUMENTS

| | | |
|---|---|---|
| 0 054 858 | 6/1982 | European Pat. Off. . |
| 2 586 913 | 3/1987 | France . |
| 2 733 749 | 11/1996 | France . |
| 2 750 048 | 12/1997 | France . |
| 2 359 399 | 6/1975 | Germany . |
| 3 843 892 | 6/1990 | Germany . |
| 4 009 097 | 9/1991 | Germany . |
| 4 133 957 | 4/1993 | Germany . |
| 19 543 988 | 5/1997 | Germany . |
| 63-169571 | 7/1988 | Japan . |
| 3 10659 | 1/1991 | Japan . |
| 1 026 978 | 4/1966 | United Kingdom . |
| 1 153 196 | 5/1969 | United Kingdom . |
| 1 159 691 | 7/1969 | United Kingdom . |
| 94/08969 | 4/1994 | WIPO . |
| 94/08970 | 4/1994 | WIPO . |
| 96/15765 | 5/1996 | WIPO . |

OTHER PUBLICATIONS

Alan R. Katritzky et al., "Isomers and Aza–analogues of Indoxyl Containing Nitrogen at a Ring–fusion Position: Coupling Reactions with Electrophiles and Attempted Oxidations", J. Heterocycl. Chem., vol. 23, No. 5, pp. 1315–1325, Sep.–Oct. 1986.
English language Derwent Abstract of DE 2 359 399, Jun. 1975.
English language Derwent Abstract of DE 3 843 892, Jun. 1990.
English language Derwent Abstract of DE 4 009 097, Sep. 1991.
English language Derwent Abstract of DE 4 133 957, Apr. 1993.
English language Derwent Abstract of DE 19 543 988, May 1997.
English language Derwent Abstract of EP 0 054 858, Jun. 1982.
English language Derwent Abstract of FR 2 586 913, Mar. 1987.
English language Derwent Abstract of FR 2 733 749, Nov. 1996.
English language Derwent Abstract of FR 2 750 048, Dec. 1997.
English language Derwent Abstract of JP 3–10659, Jan. 1991.
English language Derwent Abstract of JP 2526099 B2 Aug. 1996.

*Primary Examiner*—Caroline D. Liott
*Attorney, Agent, or Firm*—Finnegan, Henderson, Farabow, Garrett & Dunner, L.L.P.

[57] ABSTRACT

A composition for the oxidation dyeing of keratinous fibers comprising at least one imidazopyridine derivative as coupler and at least one oxidation base and the use of such an imidazopyridine derivative as a coupler, in combination with at least one oxidation base, for the oxidation dyeing of keratinous fibers and the dyeing processes employing them.

31 Claims, No Drawings

COMPOSITIONS FOR DYEING KERATINOUS FIBERS COMPRISING IMIDAZOPYRIDINE DERIVATIVES AND PROCESS

The subject-matter of the invention is a composition for the oxidation dyeing of keratinous fibers comprising at least one imidazopyridine derivative as coupler and at least one oxidation base.

It is known to dye keratinous fibers and in particular human hair with dyeing compositions comprising oxidation dye precursors, in particular ortho- or para-phenylenediamines, ortho- or para-aminophenols, or heterocyclic compounds, generally known as oxidation bases. Oxidation dye precursors or oxidation bases are colorless or weakly colored compounds which, in combination with oxidizing products, can give rise, by an oxidative coupling process, to colored and coloring compounds.

It is also known that it is possible to vary the shades obtained with these oxidation bases by combining them with couplers or coloring modifiers, the latter being selected in particular from aromatic meta-diamines, meta-aminophenols, meta-diphenols and certain heterocyclic compounds, such as indole compounds. Couplers of the imidazo[1,2-a]pyridin-2(3H)-one family are also known according to German Patent Application DE-A-4009097.

The variety of the molecules involved as oxidation bases and couplers makes it possible to obtain a rich palette of colors.

The so-called "permanent" coloring obtained by virtue of these oxidation dyes has, however, to satisfy a certain number of requirements. Thus, it must be without disadvantage toxicologically and it must make it possible to obtain shades with the desired intensity that behave well in the face of external agents (light, bad weather, washing, permanent waving, perspiration or rubbing).

The dyes must also make it possible to cover white hair and, finally, be as non-selective as possible, i.e., make it possible to obtain the smallest possible differences in coloring along the same keratinous fiber, which can in fact be differently sensitized (i.e., damaged) between its tip and its root.

The inventors have discovered that it is possible to obtain powerful novel dyes, which are not very selective, which are particularly resistant and which are capable of generating intense colorings in varied shades, by using specific imidazopyridine derivatives.

This discovery is at the basis of the present invention.

The subject-matter of the invention is thus a composition for the oxidation dyeing of keratinous fibers and in particular of human keratinous fibers, such as hair, comprising, in a medium appropriate for dyeing:
as coupler, at least one imidazopyridine derivative of following formula (I) and/or at least one of its acid addition salts:

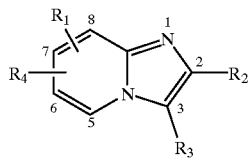

(I)

in which:
R$_1$ represents a hydrogen atom, a C$_1$–C$_4$ alkyl radical, a C$_1$–C$_4$ monohydroxyalkyl radical, a C$_2$–C$_4$ polyhydroxyalkyl radical, a (C$_1$–C$_4$)alkylamino radical, a di(C$_1$–C$_4$)alkylamino radical, a di(C$_1$–C$_4$)alkylamino (C$_1$–C$_4$)alkyl radical, a (C$_1$–C$_4$)acylamino radical, a di(C$_1$–C$_4$)acylamino radical, a (C$_1$–C$_4$) alkoxycarbonyl-(C$_1$–C$_4$)alkyl radical, a halogen atom or a nitro group;

R$_2$ and R$_3$ independently represent a hydrogen atom, a C$_1$–C$_4$ alkyl radical, a C$_1$–C$_4$ monohydroxyalkyl radical, a C$_2$–C$_4$ polyhydroxyalkyl radical, a (C$_1$–C$_4$) alkoxycarbonyl radical, a C$_1$–C$_4$ acyl radical, a halogen atom, a cyano radical, a cyano(C$_1$–C$_4$)alkyl radical, a C$_2$–C$_4$ alkynyl radical or an N-(C$_1$–C$_4$)alkylamido group;

R$_4$ denotes a hydroxyl or amino group;

and at least one oxidation base.

In the above formula (I), the C$_1$–C$_4$ alkyl and C$_1$–C$_4$ alkoxy groups may be linear or branched and, among the halogen atoms, mention may be made of chlorine, bromine, iodine and fluorine.

In the compounds of above formula (I), R$_1$ can preferably be a hydrogen atom, a C$_1$–C$_4$ alkyl radical, a C$_1$–C$_4$ monohydroxyalkyl radical, a C$_2$–C$_4$ polyhydroxyalkyl radical, a (C$_1$–C$_4$)alkylamino radical, a di(C$_1$C$_4$)alkylamino radical, a di(C$_1$–C$_4$)alkylamino(C$_1$–C$_4$)-alkyl radical, a (C$_1$–C$_4$) acylamino radical, a di(C$_1$–C$_4$)acylamino radical or a (C$_1$–C$_4$)alkoxycarbonyl(C$_1$–C$_4$)alkyl radical;

R$_2$ and R$_3$ can preferably be independently selected from a hydrogen atom, a C$_1$–C$_4$ alkyl radical, a C$_1$–C$_4$ monohydroxyalkyl radical, a C$_2$–C$_4$ polyhydroxyalkyl radical, a (C$_1$–C$_4$)alkoxycarbonyl radical, a C$_1$–C$_4$ acyl radical or an N-(C$_1$–C$_4$)alkylamido group.

The compounds of formula (I) which can be used as coupler in the dyeing composition in accordance with the invention are known compounds, the methods of preparation of which are, for example, described in the following works:
H. L. Blewitt, "Special topics in heterocyclic chemistry", edited by A. Weissberger and E. C. Taylor, published by Interscience, New York, 1977, page 117;
A. E. Tschitschibabin, Berichte, 58, 1704, 1925;
J. C. Teulade et al., Eur. J. Med. Chem., 13(3), 271, 1978;
W. W. Paudler and H. L. Blewitt, J. Org. Chem., 30 4081, 1965;
Barton D. and Ollis W. D., "Comprehensive Organic Chemistry", Vol. 4, page 400–410, published by Pergamon Press;
Fusco R., "The Chemistry of Heterocyclic Compounds, Pyrazoles, Pyrazolines, Pyrazolidines, Indazoles and Condensed Rings", 1967, published by R. H. Wiley, N.Y.;
Katritsky A., "Comprehensive heterocyclic chemistry", published by Elsevier; the disclosures of which are specifically incorporated by reference herein.

The colorings obtained with the dyeing composition in accordance with the invention have varied shades, are powerful, are not very selective and exhibit excellent properties of resistance both with respect to atmospheric agents, such as light and bad weather, and with respect to perspiration and various treatments which hair can be subjected to (shampoos, permanent deformations).

Mention may in particular be made, among the imidazopyridine derivatives of above formula (I) which can be used as couplers in the dyeing composition in accordance with the invention, of:
8-hydroxyimidazo[1,2-a]pyridine;
8-hydroxy-2-methylimidazo[1,2-a]pyridine;
8-hydroxy-2,3-dimethylimidazo[1,2-a]pyridine;
8-hydroxy-6-chloro-2-methylimidazo[1,2-a]pyridine;
8-hydroxy-3-hydroxymethyl-2-methylimidazo[1,2-a] pyridine;

8-hydroxy-7-dimethylamino-2-methylimidazo[1,2-a]
  pyridine;
(8-hydroxy-2-methylimidazo[1,2-a]pyridin-3-yl)
  acetonitrile;
8-hydroxyimidazo[1,2-a]pyridine-2,3-dicarboxylic acid bisethylamide;
the diethyl ester of 8-hydroxyimidazo[1,2-a]pyridine-2,3-dicarboxylic acid;
8-aminoimidazo[1,2-a]pyridine;
2-methyl-8-aminoimidazo[1,2-a]pyridine;
2,3-dimethyl-8-aminoimidazo[1,2-a]pyridine;
2-methyl-3-hydroxymethyl-8-aminoimidazo[1,2-a]
  pyridine;
2,7-dimethyl-8-aminoimidazo[1,2-a]pyridine;
the ethyl ester of 7-methyl-8-aminoimidazo[1,2-a]pyridine-2-carboxylic acid;
the ethyl ester of 8-aminoimidazo[1,2-a]pyridine-2-carboxylic acid;
the ethyl ester of 3-bromo-7-methyl-8-aminoimidazo[1,2-a]pyridine-2-carboxylic acid;
2-methyl-3-(prop-2-ynyl)-8-aminoimidazo[1,2-a]pyridine;
6-bromo-7-(N-ethylamino)imidazo[1,2-a]pyridine;
6-aminoimidazo[1,2-a]pyridine;
the ethyl ester of 6-aminoimidazo[1,2-a]pyridine-2-carboxylic acid;
  the ethyl ester of 5-methyl-6-aminoimidazo[1,2-a]
    pyridine-2-carboxylic acid;
the ethyl ester of 6-amino-7-methylimidazo[1,2-a]pyridine-2-carboxylic acid;
the diethyl ester of 6-aminoimidazo[1,2-a]pyridine-2,3-dicarboxylic acid;
5-aminoimidazo[1,2-a]pyridine;
3-methyl-5-aminoimidazo[1,2-a]pyridine;
2-methyl-5-aminoimidazo[1,2-a]pyridine;
2,3-dimethyl-5-aminoimidazo[1,2-a]pyridine;
the ethyl ester of 2-methyl-5-aminoimidazo[1,2-a]pyridine-3-carboxylic acid;
the ethyl ester of 5-aminoimidazo[1,2-a]pyridine-3-carboxylic acid;
3-acetyl-5-aminoimidazo[1,2-a]pyridine;
2-methyl-3-acetyl-5-aminoimidazo[1,2-a]pyridine;
and their addition salts with an acid.

The imidazopyridine derivative or derivatives of formula (I) preferably represent from approximately 0.0005 to approximately 12% by weight of the total weight of the dyeing composition in accordance with the invention and more preferably still from approximately 0.005 to approximately 6% by weight of the total weight of the dyeing composition.

The nature of the oxidation base or bases which can be used in the dyeing composition according to the invention is not critical. This or these oxidation bases are preferably selected from para-phenylenediamines, bisphenylalkylenediamines, para-aminophenols, ortho-aminophenols, heterocyclic bases, and their acid addition salts.

Mention may in particular be made, among the para-phenylenediamines which can be used as oxidation bases in the dyeing composition according to the invention, of the compounds corresponding to the following formula (II) and their acid addition salts:

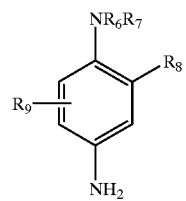

(II)

in which:
  $R_6$ represents a hydrogen atom or a $C_1-C_4$ alkyl, $C_1-C_4$ monohydroxyalkyl, $C_2-C_4$ polyhydroxyalkyl or $(C_1-C_4)$alkoxy$(C_1-C_4)$alkyl radical;
  $R_7$ represents a hydrogen atom or a $C_1-C_4$ alkyl, $C_1-C_4$ monohydroxyalkyl or $C_2-C_4$ polyhydroxyalkyl radical;
  $R_8$ represents a hydrogen atom, a halogen atom, such as a chlorine atom, or a $C_1-C_4$ alkyl, sulpho, carboxyl, $C_1-C_4$ monohydroxyalkyl or $C_1-C_4$ hydroxyalkoxy radical;
  $R_9$ represents a hydrogen atom or a $C_1-C_4$ alkyl radical.

In the above formula (II) and when $R_8$ is other than a hydrogen atom, then $R_6$ and $R_7$ preferably represent a hydrogen atom and $R_8$ is preferably identical to $R_9$ and, when $R_8$ represents a halogen atom, then $R_6$, $R_7$ and $R_8$ preferably represent a hydrogen atom.

Mention may more particularly be made, among the para-phenylenediamines of above formula (II), of para-phenylenediamine, para-toluylenediamine, 2-isopropyl-para-phenylenediamine, 2-(β-hydroxyethyl)-para-phenylenediamine, 2-(β-hydroxyethyloxy)-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 4-amino-1-[(β-methoxyethyl)amino]benzene, 2-chloro-para-phenylenediamine, 2-n-propyl-para-phenylenediamine, and their acid addition salts.

Mention may in particular be made, among the bisphenylalkylenediamines which can be used as oxidation bases in the dyeing composition according to the invention, of the compounds corresponding to the following formula (III) and their acid addition salts:

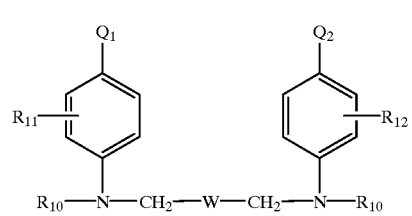

(III)

in which:
  $Q_1$ and $Q_2$, which are identical or different, represent a hydroxyl or $NHR_{13}$ radical in which $R_{13}$ represents a hydrogen atom or a $C_1-C_4$ alkyl radical;
  $R_{10}$ represents a hydrogen atom or a $C_1-C_4$ alkyl, $C_1-C_4$ monohydroxyalkyl, $C_2-C_4$ polyhydroxyalkyl or $C_1-C_4$ aminoalkyl radical in which the amino residue can be substituted;
  $R_{11}$ and $R_{12}$ independently represent a hydrogen or halogen atom or a $C_1-C_4$ alkyl radical;
  W represents a radical selected from:

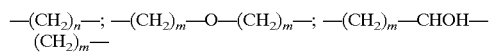

and

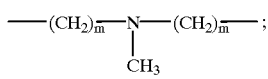

in which n is an integer ranging from 0 to 8 inclusive and m is an integer ranging from 0 to 4 inclusive.

Mention may more particularly be made, among the bisphenylalkylenediamines of above formulae (III), of N,N'-bis(β-hydroxyethyl)-N,N'-bis(4'-aminophenyl)-1,3-diamino-2-propanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, and their acid addition salts.

Among these bisphenylalkylenediamines of formula (III), N,N'-bis(β-hydroxyethyl)-N,N'-bis(4'-aminophenyl)-1,3-diamino-2-propanol or one of its acid addition salts are particularly preferred.

Mention may in particular be made, among the para-aminophenols which can be used as oxidation bases in the dyeing composition according to the invention, of the compounds corresponding to the following formula (IV) and their acid addition salts:

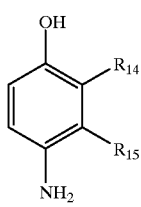

(IV)

in which:
R$_{14}$ represents a hydrogen atom or a C$_1$–C$_4$ alkyl, C$_1$–C$_4$ monohydroxyalkyl, (C$_1$–C$_4$)alkoxy(C$_1$–C$_4$)alkyl or C$_1$–C$_4$ aminoalkyl radical;
R$_{15}$ represents a hydrogen or fluorine atom or a C$_1$–C$_4$ alkyl, C$_1$–C$_4$ monohydroxyalkyl, C$_2$–C$_4$ polyhydroxyalkyl, C$_1$–C$_4$ aminoalkyl, C$_1$–C$_4$ cyanoalkyl or (C$_1$–C$_4$)alkoxy(C$_1$–C$_4$)alkyl radical;
it being understood that at least one of the R$_{13}$ and R$_{14}$ radicals represents a hydrogen atom.

Mention may more particularly be made, among the para-aminophenols of above formula (IV), of para-aminophenol, 4-amino-3-methylphenol, 4-amino-3-fluorophenol, 4-amino-3-(hydroxymethyl)phenol, 4-amino-2-methylphenol, 4-amino-2-(hydroxymethyl)phenol, 4-amino-2-(methoxymethyl)phenol, 4-amino-2-(aminomethyl)-phenol, 4-amino-2-[(β-hydroxyethyl)aminomethyl]phenol, and their acid addition salts.

Mention may in particular be made, among the ortho-aminophenols which can be used as oxidation bases in the dyeing composition according to the invention, of 2-aminophenol, 2-amino-1-hydroxy-5-methylbenzene, 2-amino-1-hydroxy-6-methylbenzene, 5-acetamido-2-aminophenol, and their acid addition salts.

Mention may more particularly be made, among the heterocyclic bases which can be used as oxidation bases in the dyeing compositions in accordance with the invention, of pyridine derivatives, pyrimidine derivatives, pyrazole derivatives, and their acid addition salts.

Mention may more particularly be made, among pyridine derivatives, of the compounds disclosed, for example, in British Patents GB 1,026,978 and GB 1,153,196, the disclosures of which are specifically incorporated herein by reference, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and their acid addition salts.

Mention may more particularly be made, among pyrimidine derivatives, of the compounds disclosed, for example, in German Patent DE 2,359,399 or Japanese Patents JP 88-169,571 and JP 91-10659 or Patent Application WO 96/15765, the disclosures of which are specifically incorporated herein by reference, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine or 2,5,6-triaminopyrimidine, and of pyrazolopyrimidine derivatives, such as those mentioned in French Patent Application FR-A-2,750,048, the disclosure of which is specifically incorporated herein by reference, and among which may be mentioned pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]-pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine, and their addition salts and their tautomeric forms, when there exists a tautomeric equilibrium, and their acid addition salts.

Mention may more particularly be made, among pyrazole derivatives, of the compounds disclosed in German Patents DE 3,843,892 and DE 4,133,957 and Patent Applications WO 94/08969, WO 94/08970, FR-A-2,733,749 and DE 195 43 988, the disclosures of which are specifically incorporated herein by reference, such as 4,5-diamino-1-methylpyrazole, 3,4-diaminopyrazole, 4,5-diamino-1-(4'-chlorobenzyl)-pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-(hydroxymethyl)pyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-(methylamino)pyrazole, 3,5-diamino-4-(β-hydroxyethyl)amino-1-methylpyrazole, and their acid addition salts.

According to the invention, the oxidation base or bases preferably represent from approximately 0.0005 to approximately 12% by weight of the total weight of the dyeing composition and more preferably still from approximately 0.005 to approximately 6% by weight of the total weight of the dyeing composition.

The dyeing composition according to the invention can also include one or more additional couplers other than the imidazopyridine derivatives of above formula (I) and/or one or more direct dyes, so as to vary or enrich with highlights the shades obtained with the oxidation bases.

The additional couplers which can be used in the composition according to the invention can be selected from couplers conventionally used in oxidation dyeing and among which may in particular be mentioned meta-phenylenediamines, meta-aminophenols, meta-diphenols and heterocyclic couplers, such as, for example, indole derivatives or indoline derivatives, and their acid addition salts.

These couplers can in particular be selected from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethyl)amino-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, and their acid addition salts.

When they are present, these additional couplers preferably represent from approximately 0.0005 to approximately 5% by weight of the total weight of the dyeing composition and more preferably still from approximately 0.005 to approximately 3% by weight of the total weight of the dyeing composition.

The acid addition salts which can be used in the context of the dyeing compositions of the invention (compounds of formula (I), oxidation bases and additional couplers) are generally selected in particular from hydrochlorides, hydrobromides, sulphates and tartrates, lactates and acetates.

The medium appropriate for dyeing (or vehicle) is generally composed of water or of a mixture of water and of at least one organic solvent, in order to dissolve the compounds which would not be sufficiently soluble in water. Mention may be made, for example, as organic solvent, of lower $C_1$–$C_4$ alkanols, such as ethanol and isopropanol, glycerol, glycols and glycol ethers, such as 2-butoxyethanol, propylene glycol, propylene glycol monomethyl ether, diethylene glycol monoethyl ether and diethylene glycol monomethyl ether, and aromatic alcohols, such as benzyl alcohol or phenoxyethanol, analogous products and their mixtures.

The solvents can be present in proportions preferably ranging from approximately 1 to approximately 40% by weight with respect to the total weight of the dyeing composition and more preferably still from approximately 5 to approximately 30% by weight.

The pH of the dyeing composition in accordance with the invention generally ranges from 3 to 12. It can be adjusted to the desired value by means of acidifying or basifying agents commonly used in dyeing keratinous fibers.

Mention may be made, among acidifying agents, by way of example, of inorganic or organic acids, such as hydrochloric acid, orthophosphoric acid, carboxylic acids, such as tartaric acid, citric acid or lactic acid, or sulphonic acids.

Mention may be made, among basifying agents, by way of example, of aqueous ammonia, alkaline carbonates, alkanolamines, such as mono-, di- and triethanolamines, and their derivatives, sodium hydroxide, potassium hydroxide and the compounds of following formula (V):

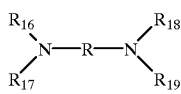

(V)

in which R is a propylene residue optionally substituted by a hydroxyl group or a $C_1$–$C_4$ alkyl radical; and $R_{16}$, $R_{17}$, $R_{18}$ and $R_{19}$ independently represent a hydrogen atom or a $C_1$–$C_4$ alkyl or $C_1$–$C_4$ hydroxyalkyl radical.

The dyeing composition according to the invention can also include various adjuvants conventionally used in hair dyeing compositions, such as anionic, cationic, non-ionic, amphoteric or zwitterionic surface-active agents or their mixtures, anionic, cationic, non-ionic, amphoteric or zwitterionic polymers or their mixtures, inorganic or organic thickening agents, antioxidizing agents, penetration agents, sequestering agents, fragrances, buffers, dispersing agents, conditioning agents, such as, for example, silicones, film-forming agents, preserving agents or opacifying agents.

Of course, a person skilled in the art will take care to choose the optional additional compound or compounds mentioned above so that the advantageous properties intrinsically attached to the dyeing composition according to the invention are not, or not substantially, detrimentally affected by the envisaged addition or additions.

The dyeing composition according to the invention can be provided in various forms, such as in the form of liquids, creams or gels, or in any other form appropriate for carrying out dyeing of keratinous fibers and in particular of human hair.

Another subject-matter of the invention is the use of the imidazopyridine derivatives of above formula (I) as coupler, in combination with at least one oxidation base, for the oxidation dyeing of keratinous fibers and in particular of human keratinous fibers, such as hair.

Another subject-matter of the invention is a process for the oxidation dyeing of keratinous fibers and in particular of human keratinous fibers, such as hair, employing the dyeing composition as defined above.

According to this process, at least one dyeing composition as defined above is applied to the fibers, the color being developed at acidic, neutral or alkaline pH using an oxidizing agent which is added to said oxidation dyeing composition at the time of application or which is present in an oxidizing composition that is applied either separately from the dye composition at the same time that said dye composition is applied to said fibers, or applied sequentially with the dye composition.

According to a particularly preferred embodiment of the dyeing process according to the invention, the dyeing composition described above is mixed, at the time of use, with an oxidizing composition comprising, in a medium appropriate for dyeing, at least one oxidizing agent present in an amount sufficient to develop a coloring. The mixture obtained is subsequently applied to the keratinous fibers and is left to stand preferably for approximately 3 to approximately 50 minutes, more preferably approximately 5 to approximately 30 minutes, after which the hair is rinsed, washed with a shampoo, rinsed again and dried.

The oxidizing agent present in the oxidizing composition as defined above can be selected from oxidizing agents conventionally used for the oxidation dyeing of keratinous fibers and among which may be mentioned hydrogen peroxide, urea hydrogen peroxide, alkali metal bromates, or persalts, such as perborates and persulphates. Hydrogen peroxide is particularly preferred.

The pH of the oxidizing composition including the oxidizing agent as defined above is such that, after mixing with the dyeing composition, the pH of the resulting composition applied to keratinous fibers preferably varies from approximately 3 to approximately 12 and more preferably still from approximately 5 to approximately 11. It is adjusted to the desired value by means of acidifying or basifying agents commonly used in dyeing keratinous fibers and as defined above.

The oxidizing composition as defined above can also include various adjuvants conventionally used in hair dyeing compositions and as defined above.

The composition which is finally applied to keratinous fibers can be provided in various forms, such as in the form of liquids, creams or gels, or in any other form appropriate for carrying out dyeing of keratinous fibers and in particular of human hair.

Another subject-matter of the invention is a dyeing multi-compartment device or kit or any other packaging system with several compartments, a first compartment of which includes the dyeing composition as defined above and a second compartment of which includes the oxidizing composition as defined above. These devices can be equipped with a means allowing the desired mixture to be deposited on the hair, such as the devices disclosed in French Patent FR-2,586,913.

The examples which follow are intended to illustrate the invention without limiting the scope thereof.

APPLICATION EXAMPLES

Examples 1 to 5 of Dyeing in Alkaline Medium

The following dyeing compositions in accordance with the invention were prepared:

| | |
|---|---|
| 8-Hydroxyimidazo[1,2-a]pyridine (coupler of formula (I)) | 0.003 mol |
| Oxidation base | 0.003 mol |
| Oleyl alcohol polyglycerolated with 2 mol of glycerol | 4.0 g |
| Oleyl alcohol polyglycerolated with 4 mol of glycerol comprising 78% of active material (A.M.) | 5.69 g A.M. |
| Oleic acid | 3.0 g |
| Oleylamine with 2 mol of ethylene oxide, sold under the tradename ETHOMEEN 012 ® by the company Akzo | 7.0 g |
| Diethylaminopropyl laurylaminosuccinamate, sodium salt, comprising 55% of A.M. | 3.0 g A.M. |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Propylene glycol monomethyl ether | 9.0 g |
| Sodium metabisulphite as an aqueous solution comprising 35% of A.M. | 0.455 g A.M. |
| Ammonium acetate | 0.8 g |
| Antioxidizing agent, sequestering agent | q.s. |
| Fragrance, preserving agent | q.s. |
| Aqueous ammonia comprising 20% of $NH_3$ | 10.0 g |
| Demineralized water q.s. | 100 g |

These compositions were prepared with the following oxidation bases B:
B1: para-Phenylenediamine
B2: para-Toluylenediamine sulphate
B3: 2-n-Propyl-para-phenylenediamine
B4: para-Aminophenol
B5: 4-Amino-3-methylphenol At the time of use, each dyeing composition described above was mixed weight for weight with a 20-volume hydrogen peroxide solution (6% by weight).

Each mixture obtained was applied for 30 minutes to locks of natural grey hair containing 90% of white hairs in the proportion of 28 g per 3 g of hair. After rinsing, washing with a standard shampoo and drying, the locks were dyed in the shades which appear in Table I below:

TABLE 1

| Example | Oxidation base | Shade |
|---|---|---|
| 1 | B1 | Ash iridescent blonde |
| 2 | B2 | Golden beige blonde |
| 3 | B3 | Grey blonde |
| 4 | B4 | Iridescent golden light blonde |
| 5 | B5 | Iridescent light blonde with golden highlight |

Examples 6 to 17 of Dyeing in Basic Medium

The following dyeing compositions in accordance with the invention were prepared:

| | |
|---|---|
| Coupler of formula (I) | 0.003 mol |
| Oxidation base | 0.003 mol |
| 96° Ethyl alcohol | 18 g |
| Sodium metabisulphite as a 35% aqueous solution | 0.68 g |
| Pentasodium salt of diethylenetriaminepentaacetic acid | 1.1 g |
| Aqueous ammonia comprising 20% of $NH_3$ | 10 g |
| Demineralized water q.s. | 100 g |

These compositions were prepared with the couplers C of formula (I) and the following oxidation bases B:
C1: 5-Aminoimidazo[1,2-a]pyridine.1 HCl
C2: 8-Aminoimidazo[1,2-a]pyridine.2HCl
B1: para-Phenylenediamine
B4: para-Aminophenol
B5: 4-Amino-3-methylphenol
B6: para-Toluylenediamine
B7: 4,5-Diamino-1,3-dimethylpyrazole.2HCl
B8: Pyrazolo[1,5-a]pyrimidine-3,7-diamine.2HCl At the time of use, each of the dyeing compositions described above was mixed weight for weight with a 20-volume hydrogen peroxide solution (6% by weight).

Each of the mixtures obtained exhibited a pH of approximately 9.8±0.2 and was applied for 30 minutes to locks of natural grey hair containing 90% of white hairs in the proportion of 28 g per 3 g of hair. After rinsing, washing with a standard shampoo and drying, the locks were dyed in the shades which appear in Table II below:

TABLE II

| Example | Coupler | Base | Shade |
|---|---|---|---|
| 6 | C1 | B1 | Red iridescent chestnut |
| 7 | C1 | B6 | Red iridescent chestnut |
| 8 | C1 | B4 | Golden light blonde |
| 9 | C1 | B7 | Bluish purple |
| 10 | C1 | B8 | Red |
| 11 | C1 | B5 | Iridescent beige light blonde |
| 12 | C2 | B1 | Red iridescent dark blonde |
| 13 | C2 | B6 | Red iridescent blonde |
| 14 | C2 | B4 | Coppery golden light blonde |
| 15 | C2 | B7 | Matte golden light blonde |
| 16 | C2 | B8 | Mahogany golden dark blonde |
| 17 | C2 | B5 | Iridescent light blonde |

Examples 18 to 29 of Dyeing in Neutral Medium

The following dyeing compositions in accordance with the invention were prepared:

| | |
|---|---|
| Coupler of formula (I) | 0.003 mol |
| Oxidation base | 0.003 mol |
| 96° Ethyl alcohol | 18 g |
| Sodium metabisulphite as a 35% aqueous solution | 0.68 g |
| Pentasodium salt of diethylenetriaminepenta-acetic acid | 1.1 g |
| Aqueous ammonia comprising 20% of $NH_3$ | 10 g |
| $K_2HPO_4/KH_2PO_4$ (1.5 M/1 M) phosphate buffer | 10 g |
| Demineralized water q.s. | 100 g |

These compositions were prepared with the couplers C of formula (I) and the following oxidation bases B:
C1: 5-Aminoimidazo[1,2-a]pyridine.1HCl
C2: 8-Aminoimidazo[1,2-a]pyridine.2HCl
B1: para-Phenylenediamine
B4: para-Aminophenol
B5: 4-Amino-3-methylphenol
B6: para-Toluylenediamine
B7: 4,5-Diamino-1,3-dimethylpyrazole.2HCl
B8: Pyrazolo[1,5-a]pyrimidine-3,7-diamine.2HCl Each of the dyeing compositions was applied to locks of natural grey hair containing 90% white hairs according to the dyeing process described above for Examples 6 to 17. Each of the mixtures obtained exhibited a pH of about 6 to 7.

The hair was dyed as shown in Table III below:

TABLE III

| Example | Coupler | Base | Shade |
|---|---|---|---|
| 18 | C1 | B1 | Toned-down deep-purple brown |
| 19 | C1 | B6 | Ash mahogany golden chestnut |
| 20 | C1 | B4 | Coppery golden light blonde |
| 21 | C1 | B7 | Pinkish bluish grey |
| 22 | C1 | B8 | Toned-down ash mahogany |
| 23 | C1 | B5 | Slightly matte golden light blonde |
| 24 | C2 | B1 | Deep-purple ash chestnut |
| 25 | C2 | B6 | Toned-down deep-purple ash chestnut |
| 26 | C2 | B4 | Golden coppery light blonde |
| 27 | C2 | B7 | Iridescent ash light blonde |
| 28 | C2 | B8 | Deep-purple chestnut |
| 29 | C2 | B5 | Golden iridescent light blonde |

We claim:

1. An oxidation dyeing composition for keratinous fibers comprising, in a medium appropriate for dyeing:

as coupler, at least one imidazopyridine derivative of formula (I) and/or at least one acid addition salt thereof:

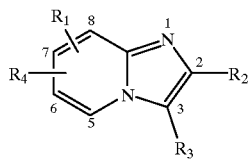

(I)

in which:

$R_1$ represents a hydrogen atom, a $C_1$–$C_4$ alkyl radical, a $C_1$–$C_4$ monohydroxyalkyl radical, a $C_2$–$C_4$ polyhydroxyalkyl radical, a ($C_1$–$C_4$)alkylamino radical, a di($C_1$–$C_4$)alkylamino radical, a di($C_1$–$C_4$) alkylamino-($C_1$–$C_4$)alkyl radical, a ($C_1$–$C_4$) acylamino radical, a di($C_1$–$C_4$)acylamino radical, a ($C_1$–$C_4$)alkoxycarbonyl($C_1$–$C_4$)alkyl radical, a halogen atom or a nitro group;

$R_2$ and $R_3$ independently represent a hydrogen atom, a $C_1$–$C_4$ alkyl radical, a $C_1$–$C_4$ monohydroxyalkyl radical, a $C_2$–$C_4$ polyhydroxyalkyl radical, a ($C_1$–$C_4$)alkoxycarbonyl radical, a $C_1$–$C_4$ acyl radical, a halogen atom, a cyano radical, a cyano ($C_1$–$C_4$)alkyl radical, a $C_2$–$C_4$ alkynyl radical or an N-($C_1$–$C_4$)alkylamido group;

$R_4$ denotes a hydroxyl or amino group; and and at least one oxidation base.

2. An oxidation dyeing composition according to claim 1, wherein said keratinous fibers are human keratinous fibers.

3. An oxidation dyeing composition according to claim 2, wherein said human keratinous fibers are hair.

4. An oxidation dyeing composition according to claim 1, wherein said halogen atom is chlorine, bromine, iodine or fluorine.

5. An oxidation dyeing composition according to claim 1, wherein $R_1$ represents a hydrogen atom, a $C_1$–$C_4$ alkyl radical, a $C_1$–$C_4$ monohydroxyalkyl radical, a $C_2$–$C_4$ polyhydroxyalkyl radical, a ($C_1$–$C_4$)alkylamino radical, a di($C_1$–$C_4$)alkylamino radical, a di($C_1$–$C_4$)alkylamino ($C_1$–$C_4$)alkyl radical, a ($C_1$–$C_4$)acylamino radical, a di($C_1$–$C_4$)acylamino radical, or a ($C_1$–$C_4$) alkoxycarbonyl-($C_1$–$C_4$)alkyl radical; and $R_2$ and $R_3$ independently represent a hydrogen atom, a $C_1$–$C_4$ alkyl radical, a $C_1$–$C_4$ monohydroxyalkyl radical, a $C_2$–$C_4$ polyhydroxyalkyl radical, a ($C_1$–$C_4$) alkoxycarbonyl radical, a $C_1$–$C_4$ acyl radical, or a N-($C_1$–$C_4$)alkylamido group.

6. An oxidation dyeing composition according to claim 1, wherein said at least one imidazopyridine derivative of formula (I) is:

8-hydroxyimidazo[1,2-a]pyridine;
8-hydroxy-2-methylimidazo[1,2-a]pyridine;
8-hydroxy-2,3-dimethylimidazo[1,2-a]pyridine;
8-hydroxy-6-chloro-2-methylimidazo[1,2-a]pyridine;
8-hydroxy-3-hydroxymethyl-2-methylimidazo[1,2-a]pyridine;
8-hydroxy-7-dimethylamino-2-methylimidazo[1,2-a]pyridine;
(8-hydroxy-2-methylimidazo[1,2-a]pyridin-3-yl)acetonitrile;
8-hydroxyimidazo[1,2-a]pyridine-2,3-dicarboxylic acid bis-ethylamide;
the diethyl ester of 8-hydroxyimidazo[1,2-a]pyridine-2,3-dicarboxylic acid;
8-aminoimidazo[1,2-a]pyridine;
2-methyl-8-aminoimidazo[1,2-a]pyridine;
2,3-dimethyl-8-aminoimidazo[1,2-a]pyridine;
2-methyl-3-hydroxymethyl-8-aminoimidazo[1,2-a]pyridine;
2,7-dimethyl-8-aminoimidazo[1,2-a]pyridine;
the ethyl ester of 7-methyl-8-aminoimidazo[1,2-a]pyridine-2-carboxylic acid;
the ethyl ester of 8-aminoimidazo[1,2-a]pyridine-2-carboxylic acid;
the ethyl ester of 3-bromo-7-methyl-8-aminoimidazo[1,2-a]pyridine-2-carboxylic acid;
2-methyl-3-(prop-2-ynyl)-8-aminoimidazo[1,2-a]pyridine;
6-bromo-7-(N-ethylamino)imidazo[1,2-a]pyridine;
6-aminoimidazo[1,2-a]pyridine;
the ethyl ester of 6-aminoimidazo[1,2-a]pyridine-2-carboxylic acid;
the ethyl ester of 5-methyl-6-aminoimidazo[1,2-a]pyridine-2-carboxylic acid;
the ethyl ester of 6-amino-7-methylimidazo[1,2-a]pyridine-2-carboxylic acid;

the diethyl ester of 6-aminoimidazo[1,2-a]pyridine-2,3-dicarboxylic acid;
5-aminoimidazo[1,2-a]pyridine;
3-methyl-5-aminoimidazo[1,2-a]pyridine;
2-methyl-5-aminoimidazo[1,2-a]pyridine;
2,3-dimethyl-5-aminoimidazo[1,2-a]pyridine;
the ethyl ester of 2-methyl-5-aminoimidazo[1,2-a]pyridine-3-carboxylic acid;
the ethyl ester of 5-aminoimidazo[1,2-a]pyridine-3-carboxylic acid;
3-acetyl-5-aminoimidazo[1,2-a]pyridine;
2-methyl-3-acetyl-5-aminoimidazo[1,2-a]pyridine;
or an acid addition salt thereof.

7. An oxidation dyeing composition according to claim 1, wherein said at least one imidazopyridine derivative of formula (I) is present in an amount ranging from 0.0005 to 12% by weight relative to the total weight of said oxidation dyeing composition.

8. An oxidation dyeing composition according to claim 7, wherein said at least one imidazopyridine derivative of formula (I) is present in an amount ranging from 0.005 to 6% by weight relative to the total weight of said oxidation dyeing composition.

9. An oxidation dyeing composition according to claim 1, wherein said at least one oxidation base is a para-phenylenediamine, a bisphenylalkylenediamine, a para-aminophenol, an ortho-aminophenol, a heterocyclic base, or an acid addition salt thereof.

10. An oxidation dyeing composition according to claim 1, wherein said at least one oxidation base is present in an amount ranging from 0.0005 to 12% by weight relative to the total weight of said oxidation dyeing composition.

11. An oxidation dyeing composition according to claim 10, wherein said at least one oxidation base is present in an amount ranging from 0.005 to 6% by weight relative to the total weight of said oxidation dyeing composition.

12. An oxidation dyeing composition according to claim 1, wherein said at least one acid addition salt is a hydrochloride, a hydrobromide, a sulphate, a tartrate, a lactate, or an acetate.

13. An oxidation dyeing composition according to claim 1, further comprising at least one additional coupler other than at least one imidazopyridine derivative of formula (I).

14. An oxidation dyeing composition according to claim 13, wherein said at least one additional coupler is present in an amount ranging from 0.0005 to 5% by weight relative to the total weight of said oxidation dyeing composition.

15. An oxidation dyeing composition according to claim 14, wherein said at least one additional coupler is present in an amount ranging from 0.005 to 3% by weight relative to the total weight of said oxidation dyeing composition.

16. An oxidation dyeing composition according to claim 1, further comprising at least one direct dye.

17. An oxidation dyeing composition according to claim 1, wherein said medium appropriate for dyeing comprises water or a mixture of water and at least one organic solvent.

18. An oxidation dyeing composition according to claim 17, wherein said at least one organic solvent is a lower $C_1$–$C_4$ alkanol, glycerol, a glycol, a glycol ether, or an aromatic alcohol.

19. An oxidation dyeing composition according to claim 17, wherein said at least one organic solvent is present in an amount ranging from 1 to 40% by weight relative to the total weight of said oxidation dyeing composition.

20. An oxidation dyeing composition according to claim 1, wherein said oxidation dyeing composition has a pH ranging from 3 to 12.

21. An oxidation dyeing composition according to claim 1, wherein said oxidation dyeing composition is in the form of a liquid, cream or gel or in any other form appropriate for dyeing keratinous fibers.

22. A method of preparing a composition for oxidation dyeing of keratinous fibers according to claim 1 comprising including in said composition a medium appropriate for dyeing, at least one imidazopyridine derivative of formula (I) and at least one oxidation base according to claim 1.

23. A process for the oxidation dyeing of keratinous fibers comprising:

applying at least one oxidation dyeing composition according to claim 1 to said keratinous fibers; and developing color at acidic, neutral or alkaline pH with at least one oxidizing agent which is added to said oxidation dyeing composition at the time of application or which is present in an oxidizing composition that is applied:
(i) separately from the dye composition at the same time that said dye composition is applied to said fibers, or
(ii) sequentially with the dye composition.

24. A process according to claim 23, wherein said keratinous fibers are human keratinous fibers.

25. A process according to claim 23, wherein said human keratinous fibers are hair.

26. A process according to claim 24, wherein said at least one oxidizing agent is hydrogen peroxide, urea hydrogen peroxide, an alkali metal bromate, or a persalt.

27. A process according to claim 26, wherein said persalt is a perborate or a persulphate.

28. A process according to claim 26, wherein said at least one oxidizing agent is hydrogen peroxide.

29. A process according to claim 23, comprising:

adding said oxidizing composition to said oxidation dyeing composition at the time of application to form a mixture, wherein said oxidizing composition comprises, in a medium appropriate for dyeing, at least one oxidizing agent present in an amount sufficient to develop color, applying said mixture to said keratinous fibers, leaving said mixture on said keratinous fibers for from 3 to 50 minutes, rinsing said keratinous fibers, and washing, rinsing and drying said keratinous fibers.

30. A process according to claim 29, wherein said mixture is left on said keratinous fibers for from 5 to 30 minutes.

31. A multi-compartment device or kit for oxidation dyeing comprising a first compartment containing at least one oxidation dyeing composition according to claim 1 and a second compartment containing at least one oxidizing composition.

* * * * *